United States Patent [19]

Jamieson et al.

[11] 4,230,716
[45] Oct. 28, 1980

[54] TREATING IMMEDIATE HYPERSENSITIVITY CONDITIONS WITH 3,5-DISUBSTITUTED HYDANTOIN DERIVATIVES

[75] Inventors: William B. Jamieson, Woking; William J. Ross, Lightwater; Robin G. Simmonds, Wokingham; John P. Verge, Henley-on-Thames, all of England

[73] Assignee: Eli Lilly Industries Limited, London, England

[21] Appl. No.: 39,077

[22] Filed: May 14, 1979

[30] Foreign Application Priority Data

May 23, 1978 [GB] United Kingdom ............ 21354/78

[51] Int. Cl.³ .................. A61K 31/415; C07D 233/78
[52] U.S. Cl. .............................. 424/273 R; 548/313; 548/314; 562/439; 562/560
[58] Field of Search ................ 548/313; 424/273 R

[56] References Cited

U.S. PATENT DOCUMENTS

| 2,626,263 | 1/1953 | Gaudry | 548/313 |
| 2,728,777 | 12/1955 | Coffman et al. | 548/313 |
| 3,395,153 | 7/1968 | Kitasaki et al. | 548/308 |

OTHER PUBLICATIONS

Rutkovskii et al. Chem. Abst. 1970, vol. 72, No. 132613y.
Hassall et al. Chem. Abst. 1972, vol. 76, No. 55564m.
Horner et al. Chem. Abst. 1953, vol. 47, col. 9923.
Knobler et al. Chem. Abst. 1967, vol. 66, No. 86001y.
Dudley et al. I. J. Heterocy. Chem. 1973, vol. 10, pp. 173-180.
Krivtsov et al. Chem. Abst. 1965, vol. 63, col. 669.
Merten et al. Chem. Abst. 1977, vol. 87, No. 102324x.
Suzuki et al. Chem. Abst. 1977, vol. 87, No. 168372t.
Ulsperger et al. Chem. Abst. 1964, vol. 60, cols. 2922-2923.
Dudley et al. II J. Pharm. Exper. Therap. 1970, vol. 175, pp. 27-37.
Knobler, Y., et al., *Tetrahedron*, 23(3), 1557-1563 (1967).
Hassall, H. et al., *Methods Enzymol.* 1971, 17 (Pt. B), 95-96, Academic Press, New York.

*Primary Examiner*—Henry R. Jiles
*Assistant Examiner*—Richard A. Schwartz
*Attorney, Agent, or Firm*—James L. Rowe; Arthur R. Whale

[57] ABSTRACT

Hydantoin compounds are described of the formula (I):

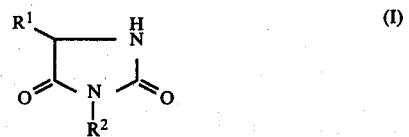

wherein $R^1$ is phenyl, $C_{1-4}$ hydroxyalkyl or carboxy $C_{1-4}$ alkyl and wherein $R_2$ is $C_{1-6}$ alkyl. The compounds are useful in the prophylactic treatment of immediate hypersensitivity diseases including asthma.

6 Claims, No Drawings

TREATING IMMEDIATE HYPERSENSITIVITY CONDITIONS WITH 3,5-DISUBSTITUTED HYDANTOIN DERIVATIVES

This invention relates to heterocyclic chemical compounds, more particularly to certain novel hydantoin derivatives which possess pharmacological activity. The invention also includes processes for preparing the compounds of the invention, pharmaceutical compositions containing the pharmacologically active compounds and methods of treatment of animals, including humans, comprising administering thereto an effective dose of the compound or compounds or of pharmaceutical compositions comprising the active compound or compounds.

According to the present invention there are provided novel hydantoin derivatives of the formula:

According to the present invention there are provided novel hydantoin derivatives of the formula:

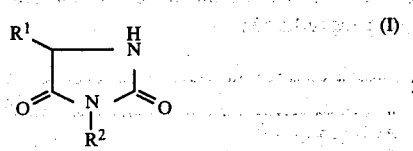

where $R^1$ is phenyl, $C_{1-4}$ hydroxyalkyl or carboxy $C_{1-4}$ alkyl and wherein $R^2$ is $C_{1-6}$ alkyl.

The term "carboxy $C_{1-4}$ alkyl" refers to $C_{1-4}$ alkyl groups substituted by a carboxylic acid function and the term embraces for example the acetic and propionic acid groups. Similarly, the term "$C_{1-4}$ hydroxyalkyl" refers to $C_{1-4}$ alkyl groups substituted by hydroxyl.

Preferably $R^1$ is hydroxymethyl and/or $R^2$ is n-butyl.

The compounds of formula (I) can be prepared by the general method described by K. H. Dudley and D. L. Biss in the *Journal of Heterocyclic Chemistry* 10 173 (1973). Briefly, this method involves the following reaction scheme:

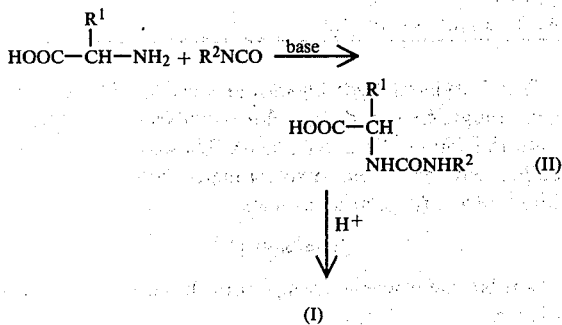

Any suitable mineral acid such as hydrochloric, sulphuric, hydrobromic or strong organic acids such as toluene sulphonic acid may be used to effect the cyclisation reaction. The cyclisation is preferably carried out at temperatures between 0° and 100° C. Any water-miscible solvent which does not react with the hydantoic acid of formula (II), such as tetrahydrofuran or dioxan, can be utilised.

Accordingly, in a further aspect of the invention there is provided a method of preparing a hydantoin of formula (I) which comprises cyclising a compound of formula (II):

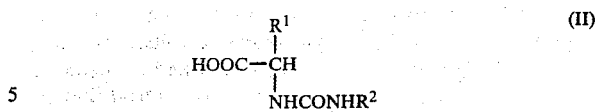

where $R^1$ and $R^2$ are as defined previously, under acid conditions.

According to a further aspect of the invention there is provided a pharmaceutical formulation which comprises a compound of formula (I) associated with a pharmaceutically-acceptable carrier therefor.

Compounds of formula (I) have been shown to be useful in the prophylactic treatment of immediate hypersensitivity diseases such as asthma in mammals. This activity has been demonstrated in guinea pigs using the "Herxheimer" test (*Journal of Physiology* (London) 117, 251 (1952)) at dosages of from 25 mg/kg to 200 mg/kg.

The compounds or compositions of the present invention may be administered by various routes, although oral administration is preferred, and for this purpose may be formulated in a variety of forms. Thus the compounds or compositions may be administered orally, rectally, topically or parenterally in the form of, for example, tablets, lozenges, sub-lingual tablets, sachets, cachets, elixirs, suspensions, suppositories, aerosols, ointments (for example, containing from 1 to 10% by weight of the active compound in a suitable base) soft and hard gelatin capsules, injection solutions and suspensions in physiologically acceptable media, and sterile packaged powders adsorbed onto a support material for making injection solutions.

Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I). Dosages of from 1 to 250 mg/kg per day, preferably 1 to 20 mg/kg of active ingredient may be administered although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of formula (I) mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material, which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidine, cetostearyl alcohol, starch, modified starches, gum acacia, calcium phosphate, cocoa butter, ethoxylated esters, oil of theobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminum, magnesium or calcium stearates, talc or mineral oil.

The following non-limitative Examples illustrate the invention.

EXAMPLE 1

3-n-Butyl-5-hydroxymethylhydantoin

DL-Serine (5.0 g) was dissolved in water (25 ml) containing sodium hydroxide (23.8 ml, 2N) and the mixture cooled to 0° C., stirred and n-butyl isocyanate (9.4 g) added. The mixture was stirred at 0° C. for 2 hours then allowed to rise to room temperature overnight, filtered and the filtrate acidified with concentrated hydrochloric acid (50 ml) and heated on a steam-bath for 2 hours. The mixture was cooled and extracted with ether (3×100 ml). Removal of the ether gave an oil which rapidly crystallised and the title product recrystallised from carbon tetrachloride as small cubes, m.p. 93° C. Yield 5.1 g=57%.

EXAMPLE 2

(1'RS,5SR)-3-n-Butyl-5-(1-hydroxyethyl) hydantoin

Allo-free DL-threonine (11.9 g, 0.1 mole) was dissolved in aqueous sodium hydroxide (50 ml, 2N) and water (50 ml), cooled to 0° C. and stirred during the addition of n-butyl isocyanate (15.0 g, 0.15 mole) over 15 minutes. The mixture was stirred for 2 hours at 0° C. and the temperature then allowed to rise to ambient overnight. The mixture was then filtered, washed with ether, acidified with concentrated hydrochloric acid, heated on a steam bath for 30 minutes and cooled. Crystals separated which were filtered off, washed with water and recrystallised from ether to yield prisms, m.p. 145° C. Yield 14.8 g=74%.

EXAMPLE 3

Similarly prepared from DL-allothreonine was (1'RS,5RS)-3-n-butyl-5-(1-hydroxyethyl) hydantoin.

EXAMPLE 4

3-(1-n-Butylimidazolidin-2,5-dion-4-yl)propionic acid n-Butyl isocyanate (7.5 g, 0.075 mole) was added dropwise to a stirred solution of DL-glutamic acid (7.35 g, 0.05 mole) in aqueous sodium hydroxide (4.0 g, in 50 ml) at 0° C. The mixture was stirred at 0° C. for 2 hours then left to rise to room temperature overnight. The mixture was filtered and the filtrate acidified with concentrated hydrochloric acid (50 ml) and heated on a steam-bath for 30 minutes. The solution was cooled whence crystals separated which were collected at the pump and recrystallised from methanol to give prisms, m.p. 130.5° C. Yield 8.7 g=76%.

EXAMPLE 5

3-n-Butylhydantoin-5-acetic acid

DL-Aspartic acid (6.65 g, 0.05 mole) in 2N-NaOH (50 ml, 2 equiv.) was cooled to 0° C. and n-butyl isocyanate (7.5 g, 0.075 mole) added during 15 minutes to the stirred solution. Stirring was continued for 2 hours and the mixture left at room temperature overnight. The mixture was then filtered, acidified with concentrated hydrochloric acid (50 ml) and heated on a steam-bath for 30 minutes. The mixture was cooled, diluted with water and continuously extracted with ether for 2½ hours. Removal of the ether gave a solid which was recrystallised from ether to yield the product as prisms, m.p. 132° C. Yield 8.8 g=82%.

EXAMPLE 6

Similarly prepared was: 3-n-Butyl-5-phenylhydantoin, b.p. 150°C./0.015 m.m.

The following Examples 7-13 illustrate pharmaceutical formulations containing the active compound 3-n-butyl-5-hydroxymethylhydantoins.

EXAMPLE 7

Soft gelatin capsules were prepared using the following ingredients:

|  | Quantity (mg/capsule) |
| --- | --- |
| Active compound | 20 |
| Propyl gallate | 0.03 |
| Fractionated Coconut Oil B.P.C. | 70 |

The above ingredients were mixed and filled into soft gelatin capsules, the main shell components of which were gelatin and glycerine.

EXAMPLE 8

Hard gelatin capsules were prepared using the following ingredients:

|  | Quantity(mg/capsule) |
| --- | --- |
| Active compound | 25 |
| Silicon dioxide (fumed) | 25 |
| Lactose | 50 |
| Butylated hydroxyanisole B.P. | 0.02 |

The butylated hydroxyanisole was dissolved in the active ingredient and the solution so formed adsorbed onto the silicon dioxide (fumed). The lactose was then added and the whole mixed. Finally, the mixture was filled into hard gelatin capsules.

EXAMPLE 9

An ointment was made up from the following ingredients:

| Active compound | 2% by weight |
| --- | --- |
| Butylated hydroxyanisole B.P. | 0.04% by weight |
| White soft paraffin | q.s. 100% |

The hydroxyanisole was dissolved in the melted paraffin and the active compound then added in, and the mixture allowed to cool.

EXAMPLE 10

A topical cream containing 1% of the compound was prepared as follows:

|  | grams: |
| --- | --- |
| Active compound | 1 |
| Cetomacrogol 1000 | 3 |
| Cetostearyl alcohol | 10 |
| Liquid Paraffin | 7 |
| Butylated hydroxyanisole B.P. | 0.04 |
| Distilled Water | to 100.0 |

The active compound was mixed with the hydroxyanisole and suspended in the liquid paraffin. The cetostearyl alcohol was added and the mixture heated to 70° C. with stirring. The cetomacrogol 1000 was then dissolved in 60 g. of water heated to 70° C. The cetostearyl alcohol and liquid paraffin active compound mixture were then poured into the aqueous cetomacrogol 1000 solution with stirring and the stirring continued until the cream was cold. The cream was then made up to weight with water and passed through a stainless steel colloid mill set at a gap of 15/1000 inch.

EXAMPLE 11

Suppositories containing 30 and 60 mg. of the compound were prepared as follows:

| Active compound | 3 g |
| --- | --- |
| Henkel base | 97 g |

The active compound was mixed with the Henkel base which had been previously melted using the minimum amount of heat possible. The mixture was then poured into suppository moulds of a nominal capacity of 1 g. or 2 g. as desired, to produce suppositories each containing 25 mg. or 50 mg. of the active compound.

EXAMPLE 12

An aerosol was prepared containing the following ingredients:

|  | Quantity per ml. |
| --- | --- |
| Active compound | 10.00 mg. |
| Propylene glycol | 10.00 mg. |
| Dichlorotetrafluoroethane (Propellant 114) | 500 mg. |
| Dichlorodifluoromethane (Propellant 12) | 900 mg. |

The active compound was mixed with the propylene glycol and the mix added to the propellant 114, the mixture cooled to −15° to −20° C. and transferred to a filling device. At the same time a mixture of propellants 114 and 12, previously cooled to −15° to −20° C. was fed into a second filling device. A metered amount of propellant from the second filling device was introduced into a stainless steel container, followed by the required amount of material from the first filling device. The valve units were then fitted and sealed to the container. These valve units were equipped with metering device so that approximately 0.15 mg. of the active compound is released by a single actuation of the valve.

EXAMPLE 13

Tablets were prepared using the following components:

| Active compound | 15.00 mg. |
| --- | --- |
| Microcrystalline Cellulose | 240.00 mg. |
| Sodium Carboxymethyl Starch | 20.00 mg. |
| Magnesium Stearate | 2.5 mg. |
| Butylated Hydroxyanisole B.P. | 0.002 mg. |

The hydroxyanisole was dissolved in the active compound, the solution adsorbed onto the microcrystalline cellulose. This was mixed with the sodium carboxymethyl starch and the magnesium stearate then mixed in. Finally, the mixture was compressed to form tablets.

We claim:

1. A hydantoin of formula (I):

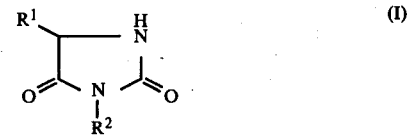

wherein $R^1$ is $C_{1-4}$ hydroxyalkyl and wherein $R^2$ is $C_{2-6}$ alkyl.

2. A hydantoin of formula (I) as claimed in claim 1, wherein $R^1$ is hydroxymethyl and $R^2$ is n-butyl.

3. A pharmaceutical formulation useful in the prophylactic chemotherapy of immediate hypersensitivity conditions such as asthma comprising a prophylactically effective amount of a hydantoin of formula (I) as claimed in claim 1 associated with a pharmaceutically-acceptable carrier therefor.

4. A pharmaceutical formulation useful in the prophylactic chemotherapy of immediate hypersensitivity conditions such as asthma comprising a prophylactically effective amount of a hydantoin of formula (I) as claimed in claim 2 associated with a pharmaceutically-acceptable carrier therefor.

5. A method of prophylactic chemotherapy of immediate hypersensitivity conditions such as asthma which comprises administering to a human susceptible to such conditions a prophylactically effective amount of a compound of the formula

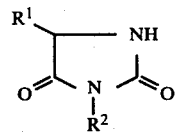

wherein $R^1$ is phenyl, $C_{1-4}$ hydroxyalkyl or carboxy $C_{1-4}$ alkyl and $R^2$ is $C_{1-6}$ alkyl.

6. A method of prophylactic chemotherapy of immediate hypersensitivity conditions such as asthma which comprises administering to a human susceptible to such conditions a prophylactically effective amount of a compound of formula (I) as claimed in claim 2.

* * * * *

UNITED STATES PATENT AND TRADEMARK OFFICE
CERTIFICATE OF CORRECTION

PATENT NO. : 4,230,716

DATED : October 28, 1980

INVENTOR(S) : William B. Jamieson, et al.

It is certified that error appears in the above-identified patent and that said Letters Patent are hereby corrected as shown below:

The name of the assignee, on the front page of the patent, "Eli Lilly Industries Limited, London, England" should read --Lilly Industries Limited, London, England--.

Signed and Sealed this

Third Day of March 1981

[SEAL]

Attest:

RENE D. TEGTMEYER

Attesting Officer     Acting Commissioner of Patents and Trademarks